(12) United States Patent
Benjamin

(10) Patent No.: US 6,217,896 B1
(45) Date of Patent: Apr. 17, 2001

(54) CONJUNCTIVAL INSERTS FOR TOPICAL DELIVERY OF MEDICATION OR LUBRICATION

(75) Inventor: William J. Benjamin, Birmingham, AL (US)

(73) Assignee: UAB Research Foundation, Birmingham, AL (US)

(*) Notice: Subject to any disclaimer, the term of this patent is extended or adjusted under 35 U.S.C. 154(b) by 0 days.

(21) Appl. No.: 09/283,957

(22) Filed: Apr. 1, 1999

(51) Int. Cl.[7] ................................. A61F 2/14; A61F 2/16
(52) U.S. Cl. .......................... 424/427; 424/420; 424/422; 424/426; 424/428; 424/429
(58) Field of Search ..................... 424/422, 427, 424/428, 420, 426, 429

(56) References Cited

U.S. PATENT DOCUMENTS

| | | | |
|---|---|---|---|
| 3,710,795 | * | 1/1973 | Higuchi et al. ................... 424/19 |
| 3,914,402 | * | 10/1975 | Shell ................................. 424/32 |
| 4,014,335 | * | 3/1977 | Arnold ............................. 128/260 |
| 4,190,642 | * | 2/1980 | Gale et al. ......................... 424/19 |
| 4,287,175 | * | 9/1981 | Katz ................................. 424/78 |
| 4,327,725 | * | 5/1982 | Cortese et al. . |
| 5,476,515 | * | 12/1995 | Kelman et al. ..................... 623/6 |

* cited by examiner

Primary Examiner—Diana Dudash
Assistant Examiner—Shahnam Sharareh
(74) Attorney, Agent, or Firm—Benjamin Aaron Adler

(57) ABSTRACT

The present invention provides an improved conjunctival insert for topical delivery of medication or lubrication into the conjunctival spaces and upon the ocular surface of human eye. Specifically, three physical designs are provided, differing by size, named "Large", "Medium" and "Small". Also provided are methods of treating ocular maladies and of lubricating or moisturizing a dry eye using the disclosed conjunctival inserts. Such inserts can also be used for veterinary practices in the cases of primates and quadrupeds.

22 Claims, 3 Drawing Sheets

CONJUNCTIVAL INSERTS FOR TOPICAL DELIVERY OF MEDICATION OR LUBRICATION

BACKGROUND OF THE INVENTION

1. Field of the Invention

The present invention relates generally to the fields of physiology, physics, drug delivery and medical treatment. More specifically, the present invention relates to non-erodable and erodable conjunctival insert designs and applications of such inserts in the topical delivery of medication and/or lubrication to the inferior and superior conjunctival spaces of the human eye or in treatment of primates and quadrupeds.

2. Description of the Related Art

Ocular inserts are devices containing medication or lubricants that are placed into the inferior or superior conjunctival sacs. Ocular inserts are perhaps more specifically called "conjunctival inserts". In theory, these devices allow more consistent release of medication or lubricant into the tear fluid over an extended time span in comparison to most other forms of topical ocular drug or lubricant delivery.

The potential advantages of inserts, especially when compared to traditional eye drops or ointments, would include the attainment of more effective therapy with reduced side effects, more efficient delivery of drugs or lubricants over a longer duration, and, perhaps, less dependence on patient compliance for maintenance and success of topical ocular therapy (1). A summary of potential advantages of the conjunctival insert as a device for topical ocular drug delivery appears in Table 1.

TABLE 1

| Potential Advantages of Ocular Inserts |
| --- |
| Steady, sustained drug release |
| Reduced overdose/underdose cycle |
| Lower total dosage required |
| Reduced short term ocular side effects, miosis, pseudomyopia |
| Reduced long term ocular side effects, preservative toxicity to ocular surface |
| Reduced systemic absorption and side effects |
| Extended duration of use |
| In contact with larger tissue surface area |
| Round-the-clock drug delivery |
| Reduced need for preservatives, liquid vehicles |
| Reversibility; take the insert out |
| Reduced dependance on patient compliance |

Several water-soluble and insoluble solid carriers have been used to topically supply medication to the eye. Gelatin wafers called "lamellae" were described as early as 1948 in the British Pharmacopeia, intended for topical application of atropine by placement beneath the eyelid (2). This general idea was revived in Moscow in the mid-1960s when rectangular inserts were cut from thin films of polyvinyl alcohol (PVA) and used to release pilocarpine into the cul-de-sac for treatment of glaucoma (3, 4). The first ocular insert produced in an oval shape was made of an insoluble form of polyvinyl alcohol soaked in pilocarpine for the slow release of medication into the inferior cul-de-sac for the treatment of glaucoma. Initially reported by Maichuk in Moscow in 1974 (5), the polyvinyl alcohol substrate appeared to have been simply punched out of a flat piece of polyvinyl alcohol, its shape similar to that which would have resulted from the use of a paper hole punch. The Maichuk inserts administered pilocarpine by first-order kinetics and the polyvinyl alcohol substrate remained in the eye until removal or expulsion (5, 6).

Additional research and development of ocular inserts were performed during the decade of the 1970s. Inserts of several different physical sizes and shapes were attempted and culminated in a few inserts that were marketed by major pharmaceutical firms. The "Lacrisert", for treatment of dry eye, is available currently in the form of a hydroxypropyl cellulose rod supplied dry and sterile in a paper/foil package (7). Individual Lacrisert rods are 3.5 mm long by 1.25 mm in diameter and are, evidently, cut from a longer dry rod of material. The unpolished ends of the Lacrisert are often jagged, but may soften and become rounded in the eye as the hydroxypropyl cellulose swells by absorbing fluid and then slowly erodes into the tear film. Thus, the hydrated Lacrisert becomes smaller with time until it erodes away or is expelled from the cul-de-sac.

"Collagen corneal shields" are contact lenses that can be used as or modified into erodable inserts. Made of treated porcine scleral collagen, the shields are in the shape of spherical contact lens shells (diameter 14.5–16.0 mm, base curves 8.8 or 9.0 mm, thickness 0.15–0.19 mm when hydrated) (7, 8). Collagen shields can be prescribed as inserts for dry eye (9) or perhaps the acute, short term treatment of ocular infections after soaking in a suitable antibiotic solution. This device is limited for delivering poorly controlled release of drug over a relatively short time, a few days at most. The erosion of these devices, although theoretically controlled by the manufacturing process, proves clinically to be unpredictable. Such device is fit only as a contact lens, i.e., to the cornea, and not as a conjunctival insert.

The "Ocusert" is considered to be the most advanced conjunctival insert available, as it is the only insert that is intended to supply medication according to zero-order kinetics. Drug release is maintained relatively constant except for an initial burst of drug release in excess of the desired dosage lasting 4–8 hours. Pilocarpine is bound to a flat, thin core of alginic acid sandwiched between two layers of ethylene vinyl acetate. The layers of ethylene vinyl acetate act as permeable barriers that allow controlled release of pilocarpine into the tear film. Two dosages are available from the manufacturer for treatment of glaucoma in slightly different elliptical dimensions: 13.4×5.7×0.3 mm and 13.0×5.5×0.5 mm (7). The elliptical, flat, thin, flexible insert is supplied dry and sterile in a paper-covered plastic storage compartment and is intended to remain in the cul-de-sac for one week until removed.

The most significant problems associated with the use of conjunctival inserts are expulsion and discomfort. At least 27% of 459 patients monitored during the wear of "Ocuserts" reported that these inserts were expelled from the eye (10). A similar percentage of patients reported that the inserts were uncomfortable (10). It is evident that conventional ocular inserts have been designed without adequate attention given to the space into which they were intended to reside. Most inserts have been tested primarily with the inferior human conjunctival sac as the place of residence, though several studies point to the superotemporal conjunctival sac as a better location for certain inserts and especially in some patients. The lack of success of human conjunctival inserts in the marketplace may have occurred because of the failure to maximally utilize the actual volume and shape that could be contained in the cul-de-sacs.

The prior art is deficient in the lack of conjunctival inserts with much improved conformity, larger drug capacity and increased stability within the sacs. The present invention fulfills this long-standing need and desire in the art.

SUMMARY OF THE INVENTION

The present invention is directed to improved conjunctival inserts and uses thereof.

In one embodiment of the present invention, there is provided a conjunctival insert of a crescent shape in the horizontal plane, comprising a central back curvature conforming to the bulbar surface; a horizontal ridge situated approximately ⅔ of the way from the top of said insert; an acute superior edge and a rounded bottom with the most inferior portion at the horizontal middle. Preferably, the back curvature has a radius of from about 12 mm to about 18 mm, and the horizontal ridge is of a crescent shape in the horizontal plane. More preferably, the rounded bottom has a radius of curvature from left to right of from about 20 mm to about 25 mm, a radius of curvature from front to back of from about 0.5 mm to about 1.0 mm. Made in three different designs varying by sizes, such conjunctival insert fits the cul-de-sac of at least 75% of adults and can be placed in either the inferior or superior cul-de-sac of an eye.

In one preferred embodiment, the inserts are made of non-erodable or erodable materials. Examples for non-erodable materials are hydrogel, more preferably silicon hydrogel, and silicon rubber. Examples of erodable materials are cellulose derivatives such as methylcellulose, sodium carboxymethyl cellulose, hydroxyethyl cellulose, hydroxypropyl cellulose and hydroxypropylmethyl cellulose; acrylates such as polyacrylic acid salts, ethylacrylates and polyacrylamides; natural products such as gelatin, collagen, alginates, pectins, tragacanth, karaya, chrondrus, agar and acacia; starch derivatives such as starch acetate, hydroxyethyl starch ethers and hydroxypropyl starch as well as synthetic derivatives such as polyvinylalcohol, poly vinylpyrrolidone, poly vinyl methyl ether, poly ethyleneoxide, neutralized Carbopol®, xanthan gum, polyester, poly ortho ester, poly anhydride, poly phosphazine, poly phosphate ester, poly caprolactone, poly hydroxybutyric acid, poly glycolic acid, poly lactic acid and mixtures thereof.

In another embodiment of the present invention, there is provided a method of delivering a drug to an individual in need of such medication, comprising the steps of placing the drug into the conjunctival insert and then contacting the individual with the drug-containing conjunctival insert by placing the insert in the inferior or superior cul-de-sac of the eye. A representative disease is glaucoma; a person having ordinary skill in this art would readily recognize other diseases which could be treated using the ocular inserts of the present invention. The ocular inserts of the present invention may contain any of a variety of useful drugs, e.g., pilocarpine or timolol; a person having ordinary skill in this art would readily recognize other drugs which could be administered using these ocular inserts.

In still yet another embodiment of the present invention, there is provided a method of lubricating or moisturizing a dry eye, comprising the steps of placing a lubricant or moisturizer into the conjunctival insert and contacting the dry eye with the lubricant- or moisturizer-containing conjunctival insert by placing the insert in the inferior or superior cul-de-sac of the eye.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
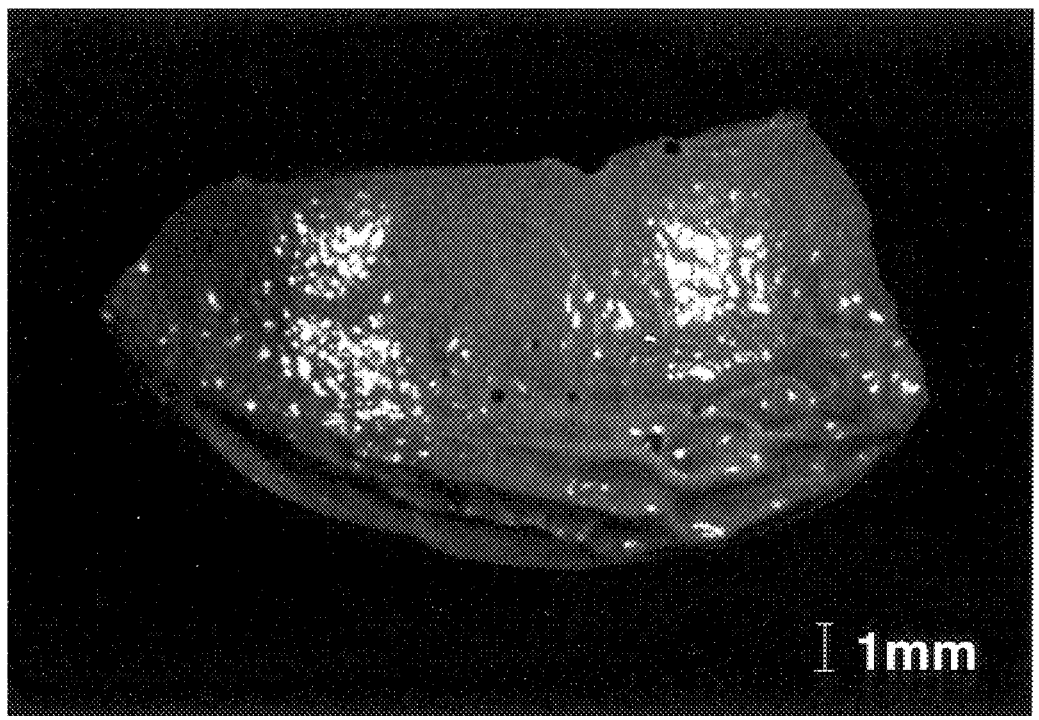
FIG. 1 is a front view of a representative conjunctival insert. Note the ridge across the lower half of the insert, peaking at about ⅔ of the way down from the top edge, that tapers nasally and temporally to blunt points. The thickest point on the insert is at the center of the ridge in the horizontal middle. This insert is taller on the right than on the left, though the design calls for the right and left halves of the insert to be equivalent in size and shape.
Figure 2:
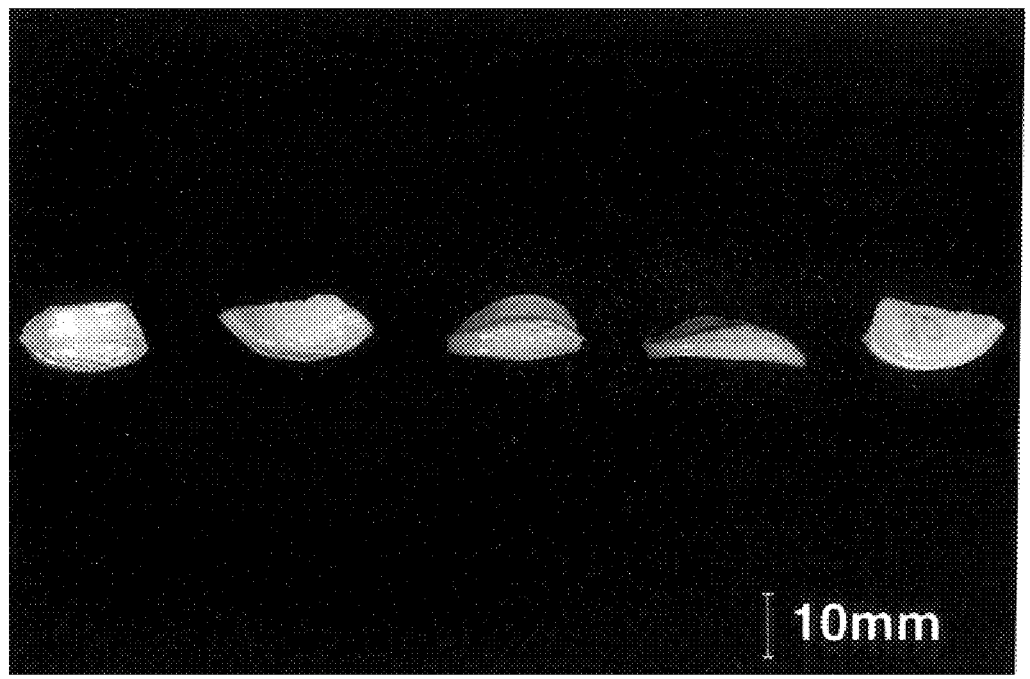
FIG. 2 shows five inserts of the same general size and shape, oriented in a frontal view on the left. Progressing from left to right are seen views from the front and superior, from the front and inferior, from below, and from the rear. Note the bulk of the volume contained in the ridge and the crescent shape conforming to the bulbar surface.
Figure 3:
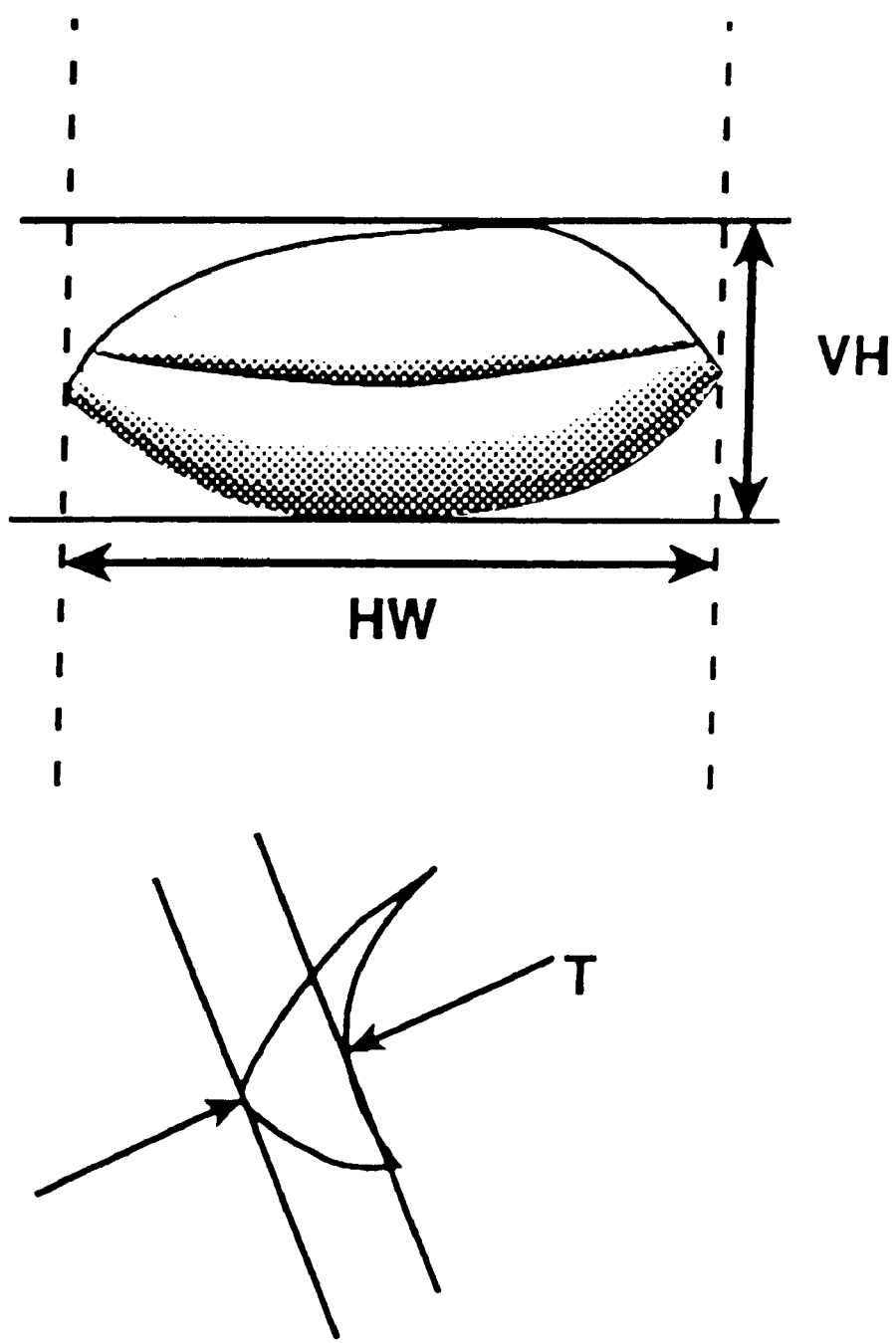
FIG. 3 is a diagram of the linear dimensions described for the invention and detailed in Table 2. HW=maximum horizontal length; VH=maximum vertical height; T=maximum thickness.

In the present invention, the following terms have the definitions set below.

As used herein, "conjunctival insert" shall refer to a device or substance intended for placement in the conjunctival space, that is to be retained in the conjunctival space for a length of time to deliver drug, medication, moisturizer and/or lubricant to the surrounding tissues.

As used herein, "cul-de-sac" shall refer to the conjunctival sac as defined below.

As used herein, "conjunctival sac" shall refer to the potential space between the bulbar and palpebral conjunctivae, and in the conjunctival fornix, that can expand into a real space by insertion of an insert or other object or substance.

As used herein, "horizontal plane" shall refer to a plane at right angles to the sagittal plane, containing the centers of the pupils of the two eyes.

As used herein, "sagittal plane" shall refer to a vertical plane containing an antero-posterior line.

As used herein, "horizontal ridge" shall refer to the thickened area of the insert running from the left to the right lateral extremes, located in the inferior half of the insert.

As used herein, "inferior edge" shall refer to the lower extreme of the insert, extending from left to right along the bottom of the insert.

As used herein, "superior edge" shall refer to the upper extreme of the insert, extending from left to right along the top of the insert.

As used herein, "horizontal length" shall refer to the linear dimension from the left-most extreme to the right-most extreme of the insert, measured along the arc of the back surface.

As used herein, "vertical height" shall refer to the linear dimension from the bottom to the top of the insert, measured at its tallest point in the facial plane.

As used herein, "thickness" shall refer to the antero-posterior linear dimension of the insert, measured at its thickest point.

As used herein, "central back curvature" shall refer to the curvature of the rear of the insert, the surface that contacts the bulbar surface, over the central surface of the insert.

As used herein, "bulbar surface" shall refer to the surface of the globe or ball of the eye.

As used herein, "rounded bottom" shall refer to the inferior edge of the insert, which is thicker than the top edge, and of a round curvature in the facial plane with radius from 20–25 mm.

As used herein, "hydrogel materials" shall refer to hydrophilic polymers that imbibe water to the extent that at least 10% of the hydrated material is composed of water.

The present invention is directed to improved non-erodable or erodable conjunctival inserts for topical delivery of medication, moisture and/or lubrication to the spaces within the conjunctival sacs surrounding the eye and to the ocular surfaces. Medications can be those directed to target tissues within and surrounding the eyes, or by systemic absorption to tissues elsewhere in the human body. Three embodiments of the inserts of the present invention were designed, differing by size, applicable to 75% or more of the human adult population. With improved moisture, flexibility and conformity, such inserts will be retained in the conjunctival spaces more consistently, more comfortably and will simultaneously be much larger than currently available inserts. In addition, the new designs will be able to hold more drug or lubricant, will contact a larger conjunctival area for such drug or lubricant delivery and will remain in the conjunctival sac for periods beyond that currently available. Furthermore, it is anticipated that the specified insert for humans will be applicable in certain veterinary practices, such as for treatment of primates and even quadrupeds.

In one embodiment of the present invention, there is provided a conjunctival insert of a crescent shape in the horizontal plane, comprising a central back curvature conforming to the bulbar surface; a horizontal ridge situated approximately ⅔ of the way from the top of said insert; a sharp superior edge and a rounded bottom with the most inferior portion at the horizontal middle. Preferably, the back curvature has a radius of from about 12 mm to about 18 mm, and the horizontal ridge is of a crescent shape in the horizontal plane. More preferably, the rounded bottom has a radius of curvature from left to right of from about 20 mm to about 25 mm, a radius of curvature from front to back of from about 0.5 mm to about 1.0 mm. Such conjunctival insert will fit the cul-de-sacs of 75% or more of the human adult population and can be placed in either the inferior or superior cul-de-sac of an eye when formed into three different sizes. Further, such conjunctival insert is made of non-erodable or erodable materials. Examples for non-erodable materials are hydrogel, more preferably silicon hydrogel, and silicon rubber. Examples of erodable materials are cellulose derivatives such as methylcellulose, sodium carboxymethyl cellulose, hydroxyethyl cellulose, hydroxypropyl cellulose and hydroxypropylmethyl cellulose; acrylates such as polyacrylic acid salts, ethylacrylates and polyacrylamides; natural products such as gelatin, collagen, alginates, pectins, tragacanth, karaya, chrondrus, agar and acacia; starch derivatives such as starch acetate, hydroxyethyl starch ethers and hydroxypropyl starch as well as synthetic derivatives such as polyvinylalcohol, poly vinylpyrrolidone, poly vinyl methyl ether, poly ethyleneoxide, neutralized Carbopol®, xanthan gum, polyester, poly ortho ester, poly anhydride, poly phosphazine, poly phosphate ester, poly caprolactone, poly hydroxybutyric acid, poly glycolic acid, poly lactic acid and mixtures thereof.

In one embodiment, the present invention is directed to an insert sized to fit in large conjunctival sacs, having the features of: a maximum horizontal length of about 26.75 mm as measured along the back surface of the insert from left to right behind the horizontal ridge; a maximum thickness of the horizontal ridge of about 2.6 mm; a vertical height of up to about 9.0 mm with the maximum height at the center of the insert and decreasing left and right; and a maximum volume of about 160 $\mu$l.

In another embodiment, the present invention is directed to an insert sized to fit in conjunctival sacs of medium capacity, having the features of: a maximum horizontal length of about 23.5 mm as measured along the back surface of the insert from left to right behind the horizontal ridge; a maximum thickness of the horizontal ridge of about 1.7 mm; a vertical height of up to about 7.9 mm with the maximum height at the center of the insert and decreasing left and right; and a maximum volume of about 110 $\mu$l.

In still another embodiment, the present invention is directed to an insert sized to fit in small conjunctival sacs, having the features of: a maximum horizontal length of about 20.25 mm as measured along the back surface of the insert from left to right behind the horizontal ridge; a maximum thickness of the horizontal ridge of about 0.8 mm; a vertical height of up to about 6.8 mm with the maximum height at the center of the insert and decreasing left and right; and a maximum volume of about 60 $\mu$l.

In yet another embodiment of the present invention, there is provided a method of delivering a drug to an individual in need of such medication, comprising the steps of placing the drug into the conjunctival insert and then contacting the individual with the drug-containing conjunctival insert by placing the insert into the inferior or superior cul-de-sac of the eye. Representative examples of the diseases are glaucoma, eye infection, eye inflammation and allergy. The ocular inserts of the present invention may contain any of a variety of useful drugs, such as an anti-glaucoma drug, an antibacterial drug, an antifungal drug, an antiviral drug, a cycloplegic drug, a steroidal drug, a non-steroidal drug, an anti-inflammatory drug or an anti-allergy drug.

In still yet another embodiment of the present invention, there is provided a method of lubricating or moisturizing a dry eye, comprising the steps of placing a lubricant or moisturizer into the conjunctival insert and contacting the conjunctival tissues of the dry eye with the lubricant- or moisturizer-containing conjunctival insert by placing the insert into the cul-de-sac of the eye.

The following examples are given for the purpose of illustrating various embodiments of the invention and are not meant to limit the present invention in any fashion.

EXAMPLE 1

Physical Design of Conjunctival Inserts

Although volumetric and linear dimensions vary between individuals, human inferior conjunctival sacs have certain common features: a crescent shape horizontally; a thick inferior horizontal ridge and a wedge-like shape sagittally (11). In order to maximally utilize the actual volume and shape that could be contained in human conjunctival sacs, the conjunctival insert shall be of a crescent shape in the horizontal plane, with the central back curvature conforming to the bulbar surface (radius of back curvature 14 mm, range 12–18 mm). Most of the volume of the device shall be contained in the inferior 50% of the shape, within a horizontal ridge situated approximately ⅔ of the way from the top of the insert and ⅓ of the way from the bottom of the insert. The maximum thickness of this ridge, being of a crescent shape in the horizontal plane, is a key dimension noted in the table, below. The front surface of the device is more curved than the back in order to attain the crescent shape. The device shall taper superiorly above the ridge, so as to situate between the tarsal plate and the globe, so that the device thins to an acute angle at its superior edge. In practicality this potentially sharp edge shall be polished so as not to scrape, cut, or otherwise injure ocular or eyelid tissue. Therefore, in the sagittal plane the device shall appear wedge-like above the ridge, such that pressure of the inferior eyelid will induce a "minus-carrier" effect and help to contain the device inside inferior cul-de sac. From the middle of the thicker volume in the ridge, the insert shall taper to blunt points nasally and temporally, such that the insert is anchored within the tissue more tightly bound at the canthi. The maximum horizontal length of the insert is a key dimension, covered in Table 2, measured along the back surface of the insert from left to right behind the ridge. At the bottom, the device is rounded from left to right (radius of curvature 22 mm, range 20–25 mm) and from front to back (radius of curvature 0.75 mm, range 0.5–1.0 mm in the middle) with the most inferior portion of the device at the horizontal middle.

TABLE 2

Dimensions of Three Designs

| DIMENSIONS | THREE DESIGNS BY SIZE | | |
|---|---|---|---|
| | LARGE (+1 S.D.) | MEDIUM (Mean) | SMALL (−1 S.D.) |
| Volume ($\mu$l) | 160 | 110 | 60 |
| Max. Horizontal Length (mm) | 26.75 | 23.5 | 20.25 |
| Max. Vertical Height (mm) | 9.0 | 7.9 | 6.8 |
| Max. Thickness (mm) | 2.6 | 1.7 | 0.8 |

From the thickest sagittal plane at its horizontal midpoint, the insert to the right shall have a shape of equal, but opposite, conformation to that existing on the left. This is so that the device will be wearable in the cul-de-sac of either eye, the left/right shape difference between conjunctival sacs of the two eyes having been show to be minimal. This will be especially true considering the flexibility and shaping conformity expected of a hydrogel insert. The vertical height of the insert, another key dimension noted in Table 2, is maximum at the center of the insert and decreases left and right to the blunt lateral extremities. This is because the device is somewhat meniscus-shaped in the facial plane, being more convex at its inferior edge and relatively flat horizontally at the superior edge.

All linear dimensions in Table 2 are determined from a "boxing system" approach, such that they are the maximum values for the dimensions listed. The dimensions of the design for an insert of "Medium" size have been derived from the mean values of a population (n=42); for a "Large" insert from the mean plus one standard deviation; and for a "Small" insert from the mean minus one standard deviation. However, the three sizes accounted for the reduced capacity of the inferior cul-de-sac in upgaze, which has a tendency to expel the inserts when made in the volume equivalent to that of the cul-de-sac in primary gaze. As a result, the parameters of the "Medium" insert were made smaller by using mean values on a smaller population (n=10) with respect to upgaze instead of the mean values for primary gaze (n=42). Similarly, the design parameters at +1 standard deviation ("Large") and at −1 standard deviation ("Small") were reduced accordingly. The volumes, thicknesses, and vertical heights have been adjusted downward so as to accommodate changes of the cul-de-sac that were observed in eyelid closure, upgaze, and downgaze. Hence, these three designs, differing by size, cover 64% of the population statistically. Similar to the fitting sets of soft contact lenses, however, a hydrogel material is likely to be of such flexibility that these three designs should adequately fit the cul-de-sacs of 75% or more of the human adult population. However, it is anticipated that significant veterinary applications could arise in the cases of primates and quadrupeds.

EXAMPLE 2

Material for Making Conjunctival Inserts

The conjunctival insert shall be made of a "soft" non-erodable and erodable material, such as a hydrogel typical of soft contact lenses, a polyvinyl alcohol or cellulose derivatives. Hydrogels, more preferably silicone hydrogels, are non-erodable materials. These hydrogel materials are biphasic and contain silicone rich domain within the hydrogel matrix. As a result, they tend to partition hydrophobic materials, such as drugs, and release them slowly. Traditional silicone rubber may also be used for the conjunctival inserts. As for erodable materials, there are a number of polymers that can be utilized. Generally, one can divide the erodable materials into two categories, those that simply dissolve with time and those that undergo chemical reactions (hydrolysis) and become soluble. Examples of erodable materials are cellulose derivatives such as methylcellulose, sodium carboxymethyl cellulose, hydroxyethyl cellulose, hydroxypropyl cellulose and hydroxypropylmethyl cellulose; acrylates such as polyacrylic acid salts, ethylacrylates and polyacrylamides; natural products such as gelatin, collagen, alginates, pectins, tragacanth, karaya, chrondrus, agar and acacia; starch derivatives such as starch acetate, hydroxyethyl starch ethers and hydroxypropyl starch as well as synthetic derivatives such as polyvinylalcohol, poly vinylpyrrolidone, poly vinyl methyl ether, poly ethyleneoxide, neutralized Carbopol®, xanthan gum, polyester, poly ortho ester, poly anhydride, poly phosphazine, poly phosphate ester, poly caprolactone, poly hydroxybutyric acid, poly glycolic acid, poly lactic acid and mixtures thereof.

The conjunctival inserts made of "soft" non-erodable and erodable materials will promote excellent comfort and, as the insert will be retained in the cul-de-sac, the hydrated materials will not dehydrate significantly as occurs will soft contact lenses (that are exposed to the outside environment). A hydrogel or other soft material is malleable to outside tissue pressures and will substantially conform to the surrounding surfaces. Hence, it is anticipated that the same designs, composed of a hydrogel or soft material, will be equally as comfortable and retention as excellent when inserted into the superior cul-de-sac instead of the inferior cul-de-sac. The orientation of the device in the superior sac will, of course, be inverted as compared to that in the inferior cul-de-sac.

Discussion

The conjunctival inserts disclosed in the present invention sit in a particular place in the eye and remain stable, specifically avoiding constant contact with the cornea and potential subsequent irritation and discomfort. That is, the inserts fit the conjunctival cul-de-sac like contact lenses fit the central ocular surface (corneal), instead of simply placing a small object in the space and hoping it would stay within the bounds of the space, free to move randomly about within the space, as has been done with all previous conjunctival inserts.

The three conjunctival inserts, differing by size, will be applicable to 75% or more of the human adult population.

This will especially be so when the designs are made of a hydrogel material such as those used in the manufacture of soft contact lenses. The moisture, flexibility, and conformity to surrounding structures associated with hydrogel materials, when produced in the above mentioned new designs, will result in conjunctival inserts that are comfortable when placed in either the inferior or superior cul-de-sacs of the eye. In addition, these inserts will be retained in the conjunctival spaces better and will simultaneously be much larger than past inserts. The new designs will be able to hold more drug or lubricant for topical delivery to the eye or to systemic targets, will contact a larger conjunctival area for such drug or lubricant delivery, and will be capable of remaining in the conjunctival sac for periods beyond that currently available. These new conjunctival inserts can further be used in concert with emerging new drug-delivery technologies to further control the treatments of many ocular maladies such as glaucoma and dry eye.

The following references were cited herewith.
1. Lamberts, *Int Ophthalmol Clin* 1980; 20: 63–77.
2. Shell, *Surv Ophthalmol* 1984; 29(2): 117–28.
3. Yakovlev et al., *Vestnik Oftal'mologii* 1966; 79: 40–42.
4. Maichuk, *Antibiotiki* 1967; 12: 432–435.
5. Maichuk et al., *Vestnik Oftal'mologii* 1974; 90: 73–76.
6. Maichuk, *Invest Ophthalmol Vis Sci* 1975; 14(2): 87–90.
7. Physician's Desk Reference for Ophthalmology, 22ed. 1994, pp235, 259–261, 263, 294–295.
8. Friedberg et al., *Ophthalmol* 1991; 98(5): 725–730.
9. Shaker et al., *CLAO J*. 1989; 15(4): 298–304.
10. Land et al., *ICIC*, 1994; 21: 212–217.
11. Cygan et al., Acta Ophthalmol. Scand., 1995; 73: 555–559.

Any patents or publications mentioned in this specification are indicative of the levels of those skilled in the art to which the invention pertains. These patents and publications are herein incorporated by reference to the same extent as if each individual publication was individually incorporated by reference.

One skilled in the art will readily appreciate that the present invention is well adapted to carry out the objects and obtain the ends and advantages mentioned, as well as those inherent therein. The present examples along with the devices, procedures, and treatments described herein are representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A conjunctival insert, wherein said insert is of a crescent shape in the horizontal plane, said insert comprising:
    a central back curvature conforming to the bulbar surface;
    a top with a sharp upper extreme;
    a horizontal ridge situated approximately two-thirds of the way from said top, wherein the upper extreme of said top above said ridge becomes progressively thinner vertically; and
    a rounded bottom with the most inferior portion at the horizontal middle.

2. The conjunctival insert of claim 1, wherein said back curvature has a radius of from about 12 mm to about 18 mm.

3. The conjunctival insert of claim 1, wherein said horizontal ridge having a crescent shape in the horizontal plane.

4. The conjunctival insert of claim 1, wherein said rounded bottom having a radius of curvature from left to right of from about 20 mm to about 25 mm, a radius of curvature from front to back of from about 0.5 mm to about 1.0 mm.

5. The conjunctival insert of claim 1, wherein said insert is sized to fit in large conjunctival sacs, having the features of:
    a horizontal length of up to about 26.75 mm, wherein said length is measured along the back surface of said insert from left to right behind said horizontal ridge;
    a thickness of said horizontal ridge of up to about 2.6 mm;
    a vertical height of up to about 9.0 mm, wherein said height being maximum at the center of said insert and decreasing left and right of said insert; and
    a volume capacity of up to about 160 μl.

6. The conjunctival insert of claim 1, wherein said insert is sized to fit in conjunctival sacs of medium capacity, having the features of:
    a horizontal length of up to about 23.5 mm, wherein said length is measured along the back surface of said insert from left to right behind said horizontal ridge;
    a thickness of said horizontal ridge of up to about 1.7 mm;
    a vertical height of up to about 7.9 mm, wherein said height being maximum at the center of said insert and decreasing left and right of said insert; and
    a volume capacity of up to about 110 μl.

7. The conjunctival insert of claim 1, wherein said insert is sized to fit in small conjunctival sacs, having the features of:
    a horizontal length of up to about 20.25 mm, wherein said length is measured along the back surface of said insert from left to right behind said horizontal ridge;
    a thickness of said horizontal ridge of up to about 0.8 mm;
    a vertical height of up to about 6.8 mm, wherein said height being maximum at the center of said insert and decreasing left and right of said insert; and
    a volume capacity of up to about 60 μl.

8. The conjunctival insert of claim 1, wherein said insert is made of materials selected from the group consisting of non-erodable and erodable materials.

9. The conjunctival insert of claim 8, wherein said non-erodable materials are selected from the group consisting of hydrogel and silicone rubber.

10. The conjunctival insert of claim 9, wherein said hydrogel is silicone hydrogel.

11. The conjunctival insert of claim 9, wherein said hydrogel contains polydimethyl siloxane units.

12. The conjunctival insert of claim 8, wherein said erodable materials are selected from the group consisting of cellulose derivatives, acrylates, natural products, starch derivatives and synthetic products.

13. The conjunctival insert of claim 12, wherein said cellulose derivatives are selected from the group consisting of methylcellulose, sodium carboxymethyl cellulose, hydroxyethyl cellulose, hydroxypropyl cellulose and hydroxypropylmethyl cellulose.

14. The conjunctival insert of claim 12, wherein said acrylates are selected from the group consisting of polyacrylic acid salts, ethylacrylates and polyacrylamides.

15. The conjunctival insert of claim 12, wherein said natural products are selected from the group consisting of gelatin, collagen, alginates, pectins, tragacanth, karaya, chrondrus, agar and acacia.

16. The conjunctival insert of claim 12, wherein said starch derivatives are selected from the group consisting of starch acetate, hydroxyethyl starch ethers and hydroxypropyl starch.

17. The conjunctival insert of claim 12, wherein said synthetic products are selected from the group consisting of polyvinylalcohol, poly vinylpyrrolidone, poly vinyl methyl ether, poly ethyleneoxide, neutralized carboxypolymethylene, xanthan gum, polyester, poly ortho ester, poly anhydride, poly phosphazine, poly phosphate ester, poly caprolactone, poly hydroxybutyric acid, poly glycolic acid, poly lactic acid and mixtures thereof.

18. The conjunctival insert of claim 1, wherein said insert is placed in either the inferior or superior cul-de-sac of an eye.

19. A method of delivering a drug to an individual's eye, comprising the steps of:

placing said drug into the conjunctival insert of claim 1; and contacting conjunctival tissues of said individual with said conjunctival insert containing said drug by placing said insert into inferior or superior cul-de-sac of the individual's eye.

20. The method of claim 19, wherein said individual having a disease selected from the group consisting of glaucoma, eye infection, eye inflammation and allergy.

21. The method of claim 19, wherein said drug is selected from the group consisting of an anti-glaucoma drug, an antibacterial drug, an antifungal drug, an antiviral drug, a cycloplegic drug, a steroidal drug, a non-steroidal drug, an anti-inflammatory drug and an anti-allergy drug.

22. A method of lubricating and/or moisturizing a dry eye, comprising the steps of:

placing a lubricant or moisturizer into the conjunctival insert of claim 1; and contacting conjunctival tissues of said dry eye with said conjunctival insert containing said lubricant or moisturizer by placing said conjunctival insert into inferior or superior cul-de-sac of said eye.

* * * * *